United States Patent [19]

Canuti et al.

[11] Patent Number: 5,646,297
[45] Date of Patent: Jul. 8, 1997

[54] PROCESS FOR PREPARATION OF 2-EQUIVALENT 4-ARYLTHIO-5-PYRAZOLONE MAGENTA COUPLERS

[75] Inventors: Anna Maria Canuti, Genoa; Enzo Coraluppi, Carcare, both of Italy

[73] Assignee: Imation Corp., St. Paul, Minn.

[21] Appl. No.: 693,837

[22] Filed: Aug. 1, 1996

[30] Foreign Application Priority Data

Sep. 18, 1995 [EP] European Pat. Off. .............. 95114620

[51] Int. Cl.$^6$ .................................................. C07D 231/52
[52] U.S. Cl. ........................................ 548/366.4; 540/579
[58] Field of Search ............................................. 548/366.4

[56] References Cited

U.S. PATENT DOCUMENTS

| | | |
|---|---|---|
| 3,227,554 | 1/1966 | Barr . |
| 3,337,344 | 8/1967 | Kimura . |
| 3,418,129 | 12/1968 | Kimura . |
| 3,519,429 | 7/1970 | Lestina . |
| 3,701,783 | 10/1972 | Barr . |
| 3,892,572 | 7/1975 | Shiba . |
| 3,907,571 | 9/1975 | Aral . |
| 3,928,044 | 12/1975 | Aral . |
| 3,935,015 | 1/1976 | Aral et al. . |
| 4,032,346 | 6/1977 | Furutachi . |
| 4,138,258 | 2/1979 | Hirose . |
| 4,199,361 | 4/1980 | Furutachi .............. 548/366.4 |
| 4,293,691 | 10/1981 | Furutachi .............. 548/366.4 |
| 4,351,897 | 9/1982 | Aoki . |
| 4,413,054 | 11/1983 | Mitsui . |
| 4,451,559 | 5/1984 | Sato et al. . |
| 4,556,630 | 12/1985 | Furutachi . |
| 4,584,266 | 4/1986 | Hirose . |
| 4,740,438 | 4/1988 | Krishnamurthy . |
| 4,853,319 | 8/1989 | Krishnamurthy . |
| 4,876,182 | 10/1989 | Buckland . |
| 4,900,657 | 2/1990 | Crawley . |
| 4,929,540 | 5/1990 | Furutachi . |
| 4,942,116 | 7/1990 | Renner . |
| 5,250,407 | 10/1993 | Kase . |
| 5,256,528 | 10/1993 | Merkel . |

FOREIGN PATENT DOCUMENTS

| | | |
|---|---|---|
| 0341204A2 | 4/1989 | European Pat. Off. . |
| 1494777 | 3/1975 | United Kingdom . |
| 2244053 | 11/1991 | United Kingdom . |
| WO88/04795 | 12/1987 | WIPO . |
| WO92/18962 | 4/1992 | WIPO . |
| WO93/02393 | 7/1992 | WIPO . |

OTHER PUBLICATIONS

Research Disclosure—Oct. 1975—#13806.
Research Disclosure—Oct. 1975—#13808.

*Primary Examiner*—Robert W. Ramsuer
*Attorney, Agent, or Firm*—Gregory A. Evearitt; Arlene K. Musser

[57] ABSTRACT

A process for preparation of 2-equivalent 4-arylthio-5-pyrazolone magenta couplers comprises the steps of:

(i) reacting a 4-equivalent 5-pyrazolone magenta coupler and a diaryldisulfide compound in the presence of 1,8-diazabicyclo-[5,4,0]-undecen-7-ene and an organic solvent to obtain a reaction product between 4-arylthio-5-pyrazolone magenta coupler and 1,8-diazabicyclo-[5,4,0]-undecen-7-ene, and (ii) converting the reaction product with an inorganic acid into the 4-arylthio-5-pyrazolone magenta coupler.

The reaction product between the 4-arylthio-5-pyrazolone magenta coupler and the 1,8-diazabicyclo-[5,4,0]-undecen-7-ene is easily formed in high yield and purity. This reaction product, which is insoluble in the reaction solvent, can be easily isolated from the reaction mixture and converted by acidification into the 2-equivalent 4-arylthio-5-pyrazolone magenta coupler in high yield and purity.

7 Claims, No Drawings

PROCESS FOR PREPARATION OF 2-EQUIVALENT 4-ARYLTHIO-5-PYRAZOLONE MAGENTA COUPLERS

FIELD OF THE INVENTION

The present invention relates to a process for preparation of 2-equivalent 4-arylthio-5-pyrazolone magenta couplers. More particularly, the present invention relates to a process for preparation of 2-equivalent 1-phenyl-3-anilino-4-phenylthio-5-pyrazolone magenta couplers.

BACKGROUND OF THE INVENTION

It is known that color images may be obtained from imagewise exposed silver halide photographic elements by development with a primary aromatic amine color developing agent in the presence of a color coupler. The oxidized color developing agent formed in the areas of silver halide development couples with the coupler to form a dye. The coupler is normally incorporated in the sensitive photographic element.

It is also known that 5-pyrazolones in which the 4-position of the pyrazolone ring is free, that is having only hydrogen substituents (4-equivalent magenta couplers), can be used as magenta couplers in color photographic elements to provide magenta dye images having useful properties. Examples of such couplers are the 4-equivalents 3-anilino-5-pyrazolone couplers described in, for example, U.S. Pat. Nos. 3,519,429, 3,907,571, 3,928,044, 3,935,015 and 4,199,361. However, 4-equivalent 5-pyrazolone couplers have a number of disadvantages, as they require four equivalents of silver to produce each molecule of dye, are sensitive to certain chemical vapors, for example formaldehyde, and have poor dye light and dye dark stability. These drawbacks can be overcome by using so-called 2-equivalent 5-pyrazolone magenta couplers in which a substituent is introduced into the coupling position (4-position) of the coupler and eliminated as a leaving group (coupling-off group or splitting-off groups) during the color development process, thus requiring only two equivalent of silver in order to produce each molecule of dye.

Among coupling-off groups known in this connection are the arylthio groups described, for example, in U.S. Pat. Nos. 3,227,554, 3,701,783, 3,935,015, 4,351,897, 4,413,054, 4,556,630, 4,584,266, 4,740,438, 4,853,319, 4,876,182, 4,900,657, 4,929,540, 4,942,116, 5,250,407, 5,262,292, and 5,256,528; WO 88/04795, 92/18902, and 93/02393; EP 341,204, and GB 1,494,777.

Methods for preparing 2-equivalent 4-arylthio-5-pyrazolone magenta couplers are described in, for example, U.S. Pat. Nos. 3,227,554, 3,701,783 and Research Disclosure 13806 (1975). The method disclosed in U.S. Pat. Nos. 3,227,554 and 3,701,783 comprises converting an arylmercaptan into the corresponding arylsulfenyl halide and reacting the arylsulfenyl halide with a 4-equivalent 5-pyrazolone magenta coupler to introduce the arylthio group into the active coupling position of the coupler. Research Disclosure 13808 describes a method which comprises adding bromine to a solution of the 4-equivalent 5-pyrazolone coupler and arylmercaptan. The methods disclosed in U.S. Pat. Nos. 3,277,554 and 3,701,783 and in Research Disclosure 1308 have been further modified by using a diaryldisulfide instead of arylmercaptan, chlorine instead of bromine or presence of a base, as disclosed in, for example, U.S. Pat. Nos. 4,351,897, 4,853,319, 4,900,657, 4,929,540, 4,942,116, and 4,876,182, EP 341,204, GB 1,494,777, and WO 92/18902. In spite of the large number of methods disclosed in the prior art, these methods of synthesizing 2-equivalent 4-arylthio-5-pyrazolone magenta couplers have disadvantages as later will be shown by Comparative Examples, and there is still the need for more convenient, efficient and expeditious methods.

U.S. Pat. No. 4,032,346 discloses a method for preparing 2-equivalent couplers comprising at the active coupling position a group of formula —S—C(=Z)—B wherein Z represents an oxygen or sulfur atom and B represents a substituent group. The method comprises reacting a 4-equivalent coupler and a disulfide of formula B—C(=Z)—S—S—C(=Z)—B in the presence of an alkali catalyst and a solvent.

U.S. Pat. No. 4,293,691 discloses a method for preparing 2-equivalent couplers comprising at the active coupling position an alkylthio group. The method comprises reacting a 4-equivalent coupler A—H, wherein A is a yellow, magenta or cyan coupler residue, with an asymmetrical disulfide of formula

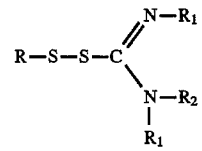

wherein R is an alkyl, a cyclic alkyl or alkenyl group, or an aralkyl group, and $R_1$ and $R_2$ are substituent groups, in the presence of a base and a solvent to obtain a 2-equivalent coupler of formula A—S—R.

The methods disclosed in U.S. Pat. Nos. 4,032,346 and 4,293,691 are not useful for the synthesis of 2-equivalent 4-arylthio-5-pyrazolones, as will later be shown by Comparative Examples.

The present invention provides an improved process for preparation of 2-equivalent 4-arylthio-5-pyrazolone magenta couplers which overcome drawbacks of prior art processes and provides a simple reaction mechanism.

SUMMARY OF THE INVENTION

A process for preparation of 2-equivalent 4-arylthio-5-pyrazolone magenta couplers comprises the steps of:

(i) reacting a 4-equivalent 5-pyrazolone magenta coupler and a diaryldisulfide compound in the presence of 1,8-diazabicyclo-[5,4,0]-undecen-7-ene and an organic solvent to obtain a reaction product between 4-arylthio-5-pyrazolone magenta coupler and 1,8-diazabicyclo-[5,4,0]-undecen-7-ene, and (ii) converting the reaction product with an inorganic acid into the 4-arylthio-5-pyrazolone magenta coupler.

It has been found in the process of the present invention that a reaction product is easily formed in high yield and purity between the 4-arylthio-5-pyrazolone magenta coupler and the 1,8-diazabicyclo-[5,4,0]-undecen-7-ene. This reaction product, which is insoluble in the reaction solvent, can be easily isolated from the reaction mixture and converted by acidification into the 2-equivalent 4-arylthio-5-pyrazolone magenta coupler in high yield and purity.

DETAILED DESCRIPTION OF THE INVENTION

The 4-equivalent 5-pyrazolone magenta couplers for use in the process of the present invention may be represented by the formula (I)

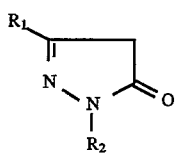

(I)

wherein $R_1$ represents an anilino group, an acylamino group or a ureido group, and $R_2$ represents a phenyl group. In more details, $R_1$ represents an anilino group such as, for example, phenylamino, o-chlorophenylamino, 2-4-dichlorophenylamino, 2,4-di-chloro-5-methoxyphenylamino, 2-chloro-5-tetradecanamidophenylamino, 2-chloro-5-[α-(2,4-di-t-amylphenoxy)-butyramido]-phenylamino, 2-chloro-5-[(3-octadecenyl)-succinimido]-phenylamino, 2-chloro-5-{α-[(3-t-butyl-4-hydroxy)-phenoxy]-tetradecan-amido}-phenylamino, an acylamino group such as, for example, acetylamino, butyramido, α-[(3-pentadecylphenoxy)butyramido]benzamido, n-tetradecanamido, α-(2,4-di-t-amylphenoxy)-butyramido, 3-[α-(2,4-di-t-amylphenoxy)butyramido]-benzamido, benzamido and 3-acetylamidobenzamido, or a ureido group such as, for example, phenylureido, methylureido, and 3-[α-(2,4-di-t-amyl-phenoxy)-butyr-amido]phenylureido, and $R_2$ represents a phenyl group such as, for example, 2,4,6-trichlorophenyl, 2,4-dichloro-6-methylphenyl,2,6-dichloro-4-methoxyphenyl, and 4-[α-(2,4-di-t-amylphenoxy)-butyramido]-phenyl.

Preferred 4-equivalent 5-pyrazolone magenta couplers for use in the process of the present invention are represented by the formula (II)

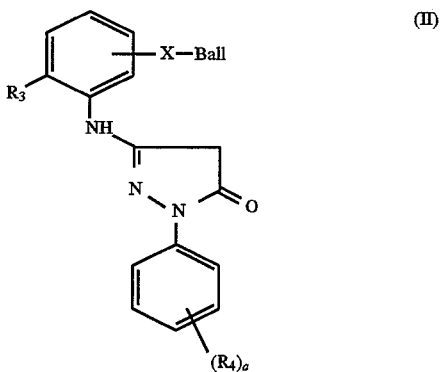

(II)

wherein a represents an integer from 1 to 5, $R_4$ represents hydrogen, alkyl, alkoxy, halogen, aryl, aryloxy, acylamino, sulfonamido, sulfamoyl, carbamoyl, arylsulfonyl, aryloxycarbonyl, alkoxycarbonyl, alkoxysulfonyl, aryloxysulfonyl, alkylureido, arylureido, nitro, cyano, hydroxyl or carboxy group, $R_3$ is halogen atom, alkyl or aryl group, X is a direct group or a linking group, Ball is a ballasting group of such size and configuration as to render a group to which it is attached non-diffusible in photographic coatings (e.g., gelatin), and when a is 2 or more, $R_4$ groups may be the same or different.

In the above formula, examples of $R_4$ include hydrogen; alkyl group, including straight or branched chain alkyl group, such as alkyl group containing 1 to 8 carbon atoms, for example methyl, trifluoromethyl, ethyl, butyl, and octyl; alkoxy group, such as an alkoxy group having 1 to 8 carbon atoms, for example methoxy, ethoxy, propoxy, 2-methoxyethoxy, and 2-ethylhexyloxy; halogen, such as chlorine, bromine, and fluorine; aryl group, such as phenyl, naphthyl, and 4-tolyl; aryloxy group, such as phenoxy, p-methoxyphenoxy, p-methylphenoxy, naphthyloxy, and tolyloxy; acylamino group, such as acetamido, benzamido, butyramido, and t-butylcarbonamido; sulfonamido group, such as methylsulfonamido, benzenesulfonamido, and p-toluylsulfonamido; sulfamoyl group, such as N-methylsulfamoyl, N,N-diethylsulfamoyl, and N,N-dimethylsulfamoyl; carbamoyl group, such as N-methylcarbamoyl, and N,N-dimethylcarbamoyl; arylsulfonyl, such as tolylsulfonyl; aryloxy-carbonyl group, such as phenoxy-carbonyl; alkoxycarbonyl group, such as alkoxy-carbonyl group containing 2 to 10 carbon atoms, for example methoxycarbonyl, ethoxycarbonyl, and benzyloxycarbonyl; alkoxysulfonyl group, such as alkoxysulfonyl group containing 2 to 10 carbon atoms, for example methoxysulfonyl, octyloxysulfonyl, and 2-ethylhexylsulfonyl; aryloxysulfonyl group, such as phenoxy-sulfonyl; alkylureido group, such as N-methylureido, N,N-dimethylureido, and N,N-dibutylureido; arylureido group, such as phenylureido; nitro, cyano, hydroxyl and carboxy group.

Examples of $R_3$ include halogen, such as chlorine, bromine, and fluorine; alkyl group, including straight or branched chain alkyl group, such as alkyl group containing 1 to 8 carbon atoms, for example methyl, trifluoromethyl, ethyl, butyl, and octyl; aryl group, such as phenyl, naphthyl, and 4-tolyl.

"Ball" is a ballasting group, i.e., an organic group of such size and configuration as to render a compound to which it is attached non-diffusible from the layer in which the compound is coated in a photographic element. Said ballasting group includes, for example, an organic hydrophobic residue having 8 to 32 carbon atoms bonded to the coupler either directly or through a divalent linking group X, such as an alkylene, imino, ether, thioether, carbonamido, sulfonamido, ureido, ester, imido, carbamoyl, and sulfamoyl group. Specific examples of suitable ballasting groups include alkyl groups (linear, branched, or cyclic), alkenyl groups, alkoxy groups, alkylaryl groups, alkylaryloxy groups, acylamidoalkyl groups, alkoxyalkyl groups, alkoxyaryl groups, alkyl groups substituted with an aryl group or a heterocyclic group, aryl groups substituted with an aryloxyalkoxycarbonyl group, and residues containing both an alkenyl or alkenyl long-chain aliphatic group and a carboxy or sulfo water-soluble group, as described, for example, in U.S. Pat. Nos. 3,337,344, 3,418,129, 3,892,572, 4,138,258, and 4,451,559, and in GB 1,494,777.

When the term "group" or "residue" is used in this invention to describe a chemical compound or substituent, the described chemical material includes the basic group or residue and that group or residue with conventional substitution. Where the term "moiety" is used to describe a chemical compound or substituent, only the unsubstituted chemical material is intended to be included. For example, "alkyl group" includes not only such alkyl moiety as methyl, ethyl, butyl, octyl, stearyl, etc., but also moieties bearing substituent groups such as halogen cyano, hydroxyl, nitro, amino, carboxylate, etc. On the other hand, "alkyl moiety" includes only methyl, ethyl, stearyl, cyclohexyl, etc.

According to the step (i) of the process of the present invention, a 4-equivalent 5-pyrazolone magenta coupler is reacted with a diaryldisulfide compound. Diaryldisulfide compounds may be represented by the formula (III)

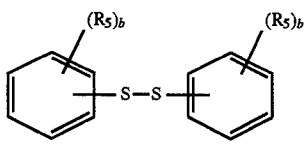

wherein $R_5$ represents a hydrogen atom, alkyl group, including straight or branched chain alkyl group, such as alkyl group containing 1 to 8 carbon atoms, for example methyl, trifluoromethyl, ethyl, butyl, and octyl; alkoxy group, such as an alkoxy group having 1 to 8 carbon atoms, for example methoxy, ethoxy, propoxy, 2-methoxyethoxy, and 2-ethylhexyloxy; halogen, such as chlorine, bromine, and fluorine; aryl group, such as phenyl, naphthyl, and 4-tolyl; aryloxy group, such as phenoxy, p-methoxyphenoxy, p-methylphenoxy, naphthyloxy, and tolyloxy; acylamino group, such as acetamido, benzamido, butyramido, and t-butylcarbonamido; sulfonamido group, such as methylsulfonamido, benzenesulfonamido, and p-toluylsulfonamido; sulfamoyl group, such as N-methylsulfamoyl, N,N-diethylsulfamoyl, and N,N-dimethylsulfamoyl; carbamoyl group, such as N-methylcarbamoyl, and N,N-dimethylcarbamoyl; arylsulfonyl, such as tolylsulfonyl; aryloxycarbonyl group, such as phenoxycarbonyl; alkoxycarbonyl group, such as alkoxycarbonyl group containing 2 to 10 carbon atoms, for example methoxycarbonyl, ethoxycarbonyl, and benzyloxycarbonyl; alkoxysulfonyl group, such as alkoxysulfonyl group containing 2 to 10 carbon atoms, for example methoxysulfonyl, octyloxysulfonyl, and 2-ethylhexylsulfonyl; aryloxysulfonyl group, such as phenoxysulfonyl; alkylureido group, such as N-methylureido, N,N-dimethylureido, and N,N-dibutylureido; arylureido group, such as phenylureido; nitro, cyano, hydroxyl and carboxy group, b represents an integer from 1 to 5, and when m represents 2 or more, each $R_5$ may be the same or different.

Preferred diaryldisulfide compounds are represented by the formula (IV)

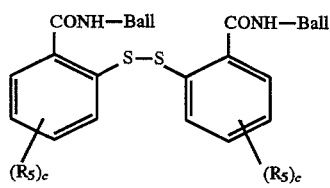

wherein $R_5$ represents a hydrogen atom or a substitute as defined for formula (III) above, c represents an integer from 1 to 4, Ball represents a ballasting group such as defined for formula (II) above, and when c represents 2 or more, each $R_6$ may be the same or different.

The reaction of diaryldisulfide compounds and 4-equivalent 5-pyrazolone magenta couplers of step (i) is carried out in the presence of 1,8-diazabicyclo-[5,4,0]-undecen-2-ene of formula

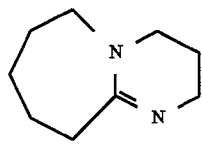

and an organic solvent. The solvents useful in step (i) are those organic liquids in which the reactants and the 1,8-diazabicyclo-[5,4,0]-undecen-2-ene are highly soluble over a wide range of temperatures, and in which, on the contrary, the adducts between formed 2-equivalent 4-arylthio-5-pryrazolone magenta couplers and 1,8-diazabicyclo-[5,4,0]-undecen-2-ene are not soluble. Representative organic liquids which are useful in this invention include ethylacetate, dimethylformamide, acetone and mixtures thereof. The reaction is completed in a short time (less than one hour) at low reaction temperatures (e.g., 40° to 70° C.). Typically, the organic solvent is the major component by volume of the reaction mixture, such as, for example, 80 to 90 percent by volume. Optionally, an additional effective amount of solvent may be added during the reaction to maintain the reaction mixture in a readily stirrable condition. At end of the reaction, the mixture is cooled at room temperature and the reaction product is recovered from the remaining mixture by filtration or centrifugation. A suitable molar ratio of the diarydisulfides to the 4-equivalent 5-pyrazolone magenta couplers is 1:1 and a suitable molar ratio of 1,8-diazabicyclo-[5,4,0]-undecen-2-ene to the 4-equivalent 5-pyrazolone magenta couplers is 2:1.

The reaction product between the 2-equivalent 4-arylthio-5-pyrazolone magenta coupler and 1,8-diazabicyclo-[5,4,0]-undecen-2-ene is a salt between a base (i.e., 1,8-diazabicyclo-[5,4,0]-undecen-2-ene) and the magenta coupler, and its structure has been confirmed by NMR and elemental analysis. It is believed that one proton is transferred by the magenta coupler to the base, with the resulting negative charge being delocalized on the coupler molecule.

As a subsequent step (ii) in the process of the present invention, the reaction product between 2-equivalent 4-arylthio-5-pryrazolone magenta couplers and 1,8-diazabicyclo-[5,4,0]-undecen-2-ene is converted with an inorganic acid into the 2-equivalent 4-arylthio-5-pyrazolone magenta coupler. A suitable conversion procedure comprises dissoving the reaction product in an organic solvent in which the reaction product is soluble, pouring the solution into an aqueous solution of an inorganic acid, such as hydrochloric acid, recovering the precipitated 2-equivalent 4-arylthio-5-pyrazolone magenta coupler by filtration or centrifugation and, if desired, subjecting to washing and crystallization from an organic solvent before drying. Suitable solvents for dissolving the reaction product include aliphatic alcohols having 1 to 4 carbon atoms, such as methanol and ethanol, taken alone or in combination with lower amounts, such as 20 to 30% by volume, of dimethylformamide.

According to the process of the present invention, 2-equivalent 5-pyrazolone magenta couplers having a 4-arythio group can be easily prepared in high yield and purity through the intermediate reaction product between 2-equivalent 4-arylthio-5-pyrazolone magenta couplers and 1,8-diazabicyclo-[5,4,0]-undecen-2-ene which is isolated in high yield and purity from the step (i), without the need of conventional extraction, drying, concentration and crystallization techniques of the prior art methods.

2-Equivalent 4-arylthio-5-pyrazolone magenta couplers which can be synthetized with the process of the present invention may be represented by the formula (V)

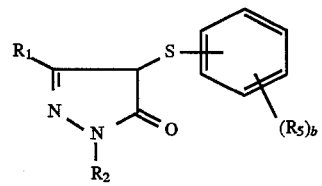

wherein $R_1$, $R_2$, $R_5$ and b are as defined for formulas (I) and (III).

Preferred 2-equivalent 4-arylthio-5-pyrazolone magenta couplers which can be synthetized with the process of the present invention may be represented by the formula (VI)

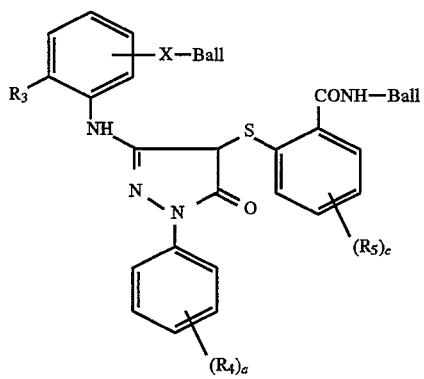

(VI)

wherein $R_3$, $R_4$, X, Ball, a and c are as defined for formulas (II) and (IV).

Illustrative examples of 2-equivalent 4-arylthio-5-pyrazolone magenta couplers represented by formula (v) are as follows.

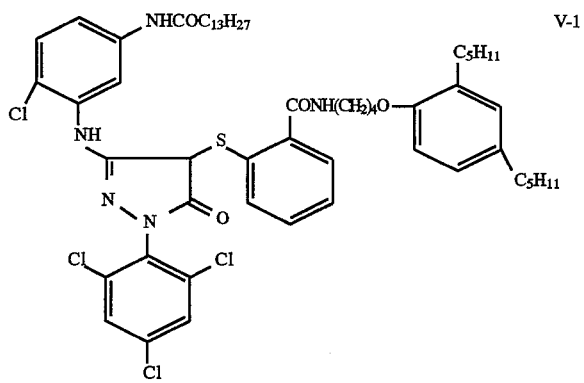

V-1

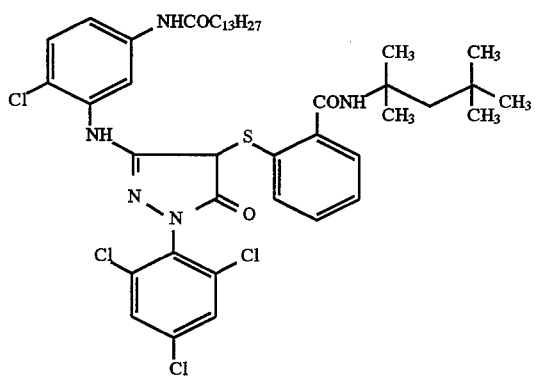

V-2

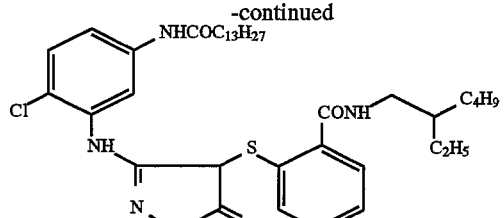

V-3

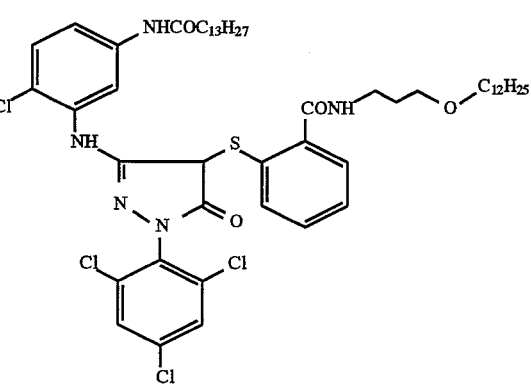

V-4

Other illustrative couplers include:

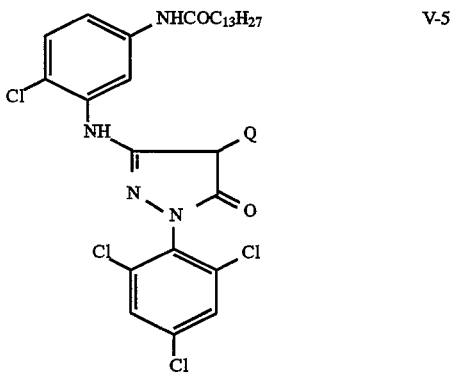

V-5

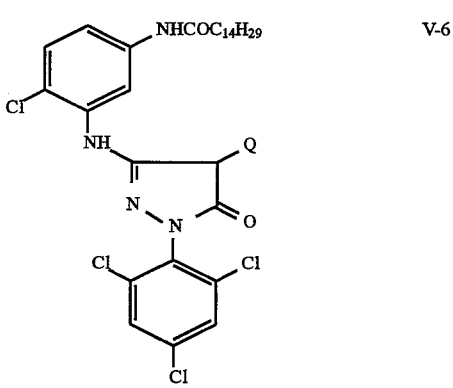

V-6

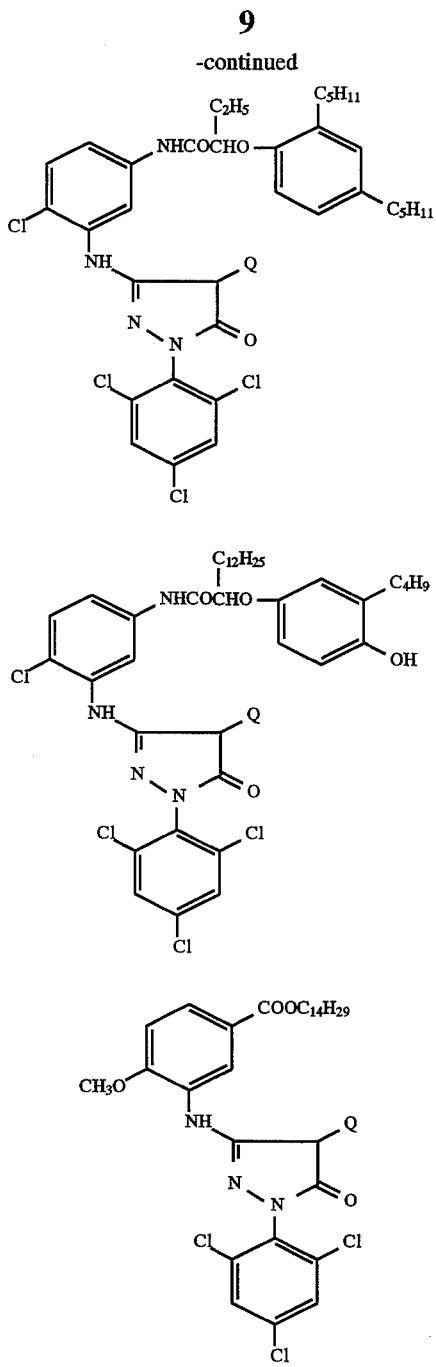

wherein Q represents a coupling-off group according to the invention.

Illustrative coupling-off groups Q are as follows:

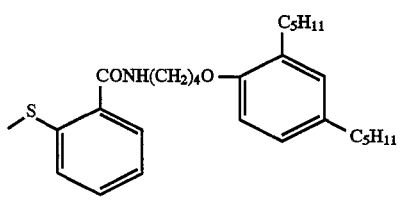

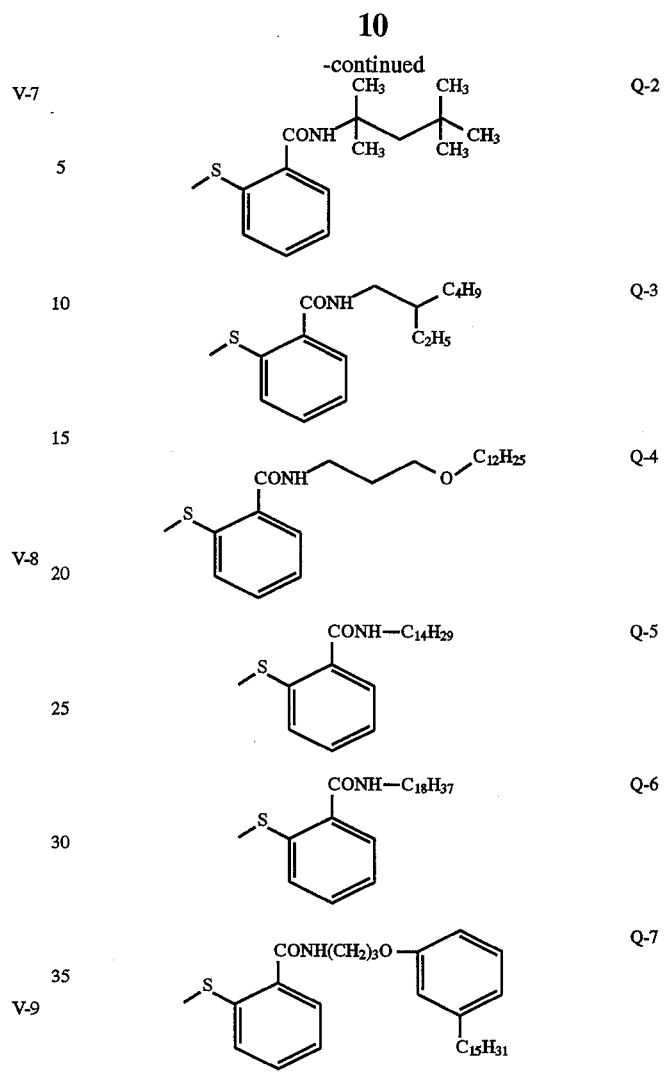

The invention is further illustrated by the following examples, but the process of this invention is not limited to these examples.

EXAMPLE 1

Preparation of 1-(2,4,6-trichlorophenyl)-3-(2-chloro-5-tetradecanamido)-4-{[2-(2,4-di-t-amylphenoxy)-butylcarbamoyl]-phenylthio}-5-pyrazolone (Coupler V-1)

45 g of 2.2'-dithiodibenzoic acid were added to 64.33 ml of thionyl chloride. Under stirring, the solution was refluxed for 3 hours and, after evaporation of half the total volume of the solvent, 120 ml of dry heptane were added. A pale yellow-brown solid was collected by filtration and dried overnight under vacuum to obtain 2,2'-dithiodibenzoyl chloride in 80% yield. The structure was confirmed by NMR and the purity by acid/base titration.

42 g of 2,2'-dithiodibenzoyl chloride were suspended in 250 ml acetone and added dropwise with 74 g of 2,4-di-tert.-amylphenoxybutylamine dissolved in 500 ml of acetone. The temperature of the solution was raised to 40° C. Then, 36 g of triethylamine were added dropwise. The suspension was poured in 2,000 ml of water, the precipitate was filtered, washed with ethanol and crystallized from ethanol. The yield was 75% of the intermediate compound having the formula:

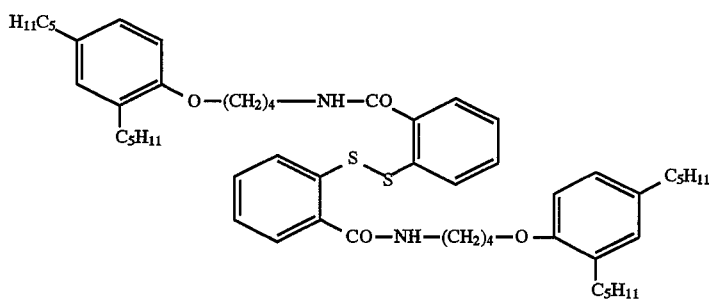

whose structure was confirmed by NMR and elemental analysis:
Found: % C=73.29% H=8.60% N=3.56% S=7.75
Required: % C=73.59% H=8.69% N=3.18% S=7.28

70 g of the intermediate compound above and 48.8 g of the 4-equivalent magenta coupler of formula

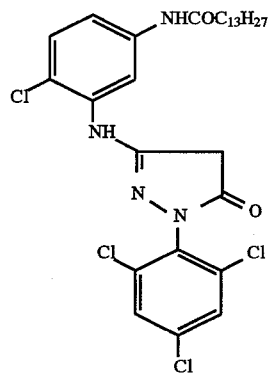

were added to 592 g of ethylacetate under stirring and the mixture was warmed to 40° C. to obtain a solution. Then, 24 g of 1,8-diazabicyclo-[5,4,0]-undecen-2-ene were added. After 15 minutes, a white solid precipitated. The suspension was heated at 60° C. and then cooled at room temperature. The solid reaction product was collected by filtration, washed with ethylacetate and dried. The yield was 86 g (90% by weight). The molar ratio of disulfide B to magenta coupler A and 1,8-diazabicyclo-[5,4,0]-undecen-2-ene was 1:1:2. The structure of the reaction product in the form of a salt between coupler V-1 and 1,8-diazabicyclo-[5,4,0]-undecen-2-ene was confirmed by NMR and elemental analysis:

Found: % C=64.60 % H=7.50 % N=8.11 % S=2.60
Required: % C=64.72 % H=7.44 % N=8.13 % S=2.66

86 g of the intermediate reaction product above were added to 257 ml of a 80% by volume methanol and 29% by volume dimethylformamide solution. A solution was obtained at room temperature. About 2 g of Celite™ absorbent were added to the solution. Then, the solution was filtered and poured into 2.5 liters of water brought at pH 1 with concentrated hydrochloric acid cooled at 10°–15° C. The white solid obtained was collected by filtration, washed with water until neutrality and dried. The yield of coupler V-1 was 90% by weight. The structure was confirmed by NMR and the purity was confirmed by acid/base titration resulting 99%. The results of the elemental analysis were:
Found: % C=63.76 % H=7.09 % N=6.84 % S=2.67
Required: % C=63.81 % H=6.98 % N=6.64 % S=3.04

The same process was carried out using other bases, such as 1,1,3,3-tetramethylguanidine, sodium acetate and 1,4-diazabicyclo-[2,2,2]-octane, but the reaction did not appreciably occur.

COMPARATIVE EXAMPLE 1

A solution of 7.52 g of bromine in 50 ml of dimethylformamide was added dropwise to a solution of 35.02 g of the magenta coupler A and 26.43 g of diaryldisulfide compound B in 210 ml of dimethylformamide under stirring. Stirring was continued for 5 hours at 60° C., then at room temperature overnight. The mixture was poured in ice water. The crude product was collected and dried. It was not possible to isolate a pure product by crystallization, but only by chromatography on silica gel (ethylacetate/methylene chloride) on a small scale with a yield of 75%. The molar ratio of the disulfide B to the magenta coupler A and bromine was 1:1.9:1.6.

COMPARATIVE EXAMPLE 2

Sulfuryl chloride (0.63 g) in methylene chloride (7.5 ml) was added dropwise and under stirring to diaryldisulfide compound B (4.13 g) in methylene chloride (25 ml). After stirring for three hours at room temperature, magenta coupler A (5.57 g) in dimethylformamide (25 ml) and triethylamine (1.3 ml) were added to the methylene chloride solution above. The mixture was stirred at room temperature for 48 hours. At this stage, unreacted compounds were still found in appreciable amounts on a thin layer chromatography. The molar ratio of disulfide compound B to magenta coupler A and triethylamine was 1:1.9:2.

The same negative results were obtained using other bases, such as 1,1,3,3-teramethylguanidine and 1,8-diazabicyclo-[5,4,0]-undecen-2-ene, and other solvents, such as toluene and ethylacetate.

We claim:

1. A process for preparation of 2-equivalent 4-arylthio-5-pyrazolone magenta couplers which comprises the steps of:

(i) reacting a 4-equivalent 5-pyrazolone magenta coupler and a diaryldisulfide compound in the presence of 1,8-diazabicyclo-[5,4,0]-undecen-7-ene and an organic solvent to obtain a reaction product between 4-arylthio-5-pyrazolone magenta coupler and 1,8-diazabicyclo-[5,4,0]-undecen-7-ene, and (ii) converting the reaction product with an inorganic acid into the 4-arylthio-5-pyrazolone magenta coupler.

2. The process of claim 1, wherein the 4-equivalent 5-pryrazolone magenta coupler is represented by the formula

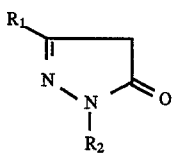

wherein $R_1$ represents an anilino group, an acylamino group or a ureido group, and $R_2$ represents a phenyl group.

3. The process of claim 1, wherein the 4-equivalent 5-pyrazolone magenta coupler is represented by the formula

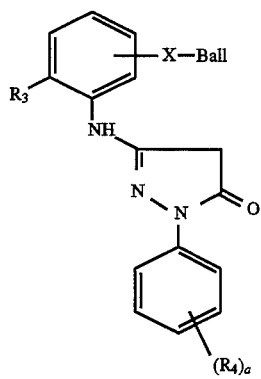

wherein a represents an integer from 1 to 5, $R_4$ represents hydrogen, alkyl, alkoxy, halogen, aryl, aryloxy, acylamino, sulfonamido, sulfamoyl, carbamoyl, arylsulfonyl, aryloxycarbonyl, alkoxycarbonyl, alkoxysulfonyl, aryloxysulfonyl, alkylureido, arylureido, nitro, cyano, hydroxyl or carboxy group, $R_3$ is halogen atom, alkyl or aryl group, X is a direct group or a linking group, Ball is a ballasting group of such size and configuration as to render a compound to which it is attached non-diffusible in photographic coatings, and when a is 2 or more, $R_4$ groups may be the same or different.

4. The process of claim 1, wherein the diaryldisulfide compound is represented by the formula

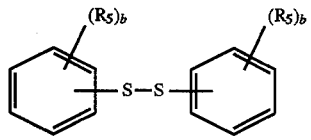

wherein $R_5$ represents hydrogen, alkyl, alkoxy, halogen, aryl, aryloxy, acylamino, sulfonamido, sulfamoyl, carbamoyl, arylsulfonyl, aryloxycarbonyl, alkoxycarbonyl, alkoxysulfonyl, aryloxysulfonyl, alkylureido, arylureido, nitro, cyano, hydroxyl or carboxy group, b represents an integer from 1 to 5, and when b represents 2 or more, each $R_5$ may be the same or different.

5. The process of claim 1, wherein the diaryldisulfide compound is represented by the formula

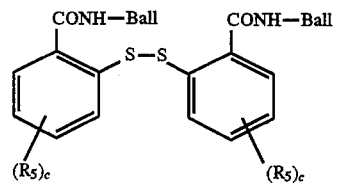

wherein $R_5$ represents hydrogen, alkyl, alkoxy, halogen, aryl, aryloxy, acylamino, sulfonamido, sulfamoyl, carbamoyl, arylsulfonyl, aryloxycarbonyl, alkoxycarbonyl, alkoxysulfonyl, aryloxysulfonyl, alkylureido, arylureido, nitro, cyano, hydroxyl or carboxy group, c represents an integer from 1 to 4, Ball represents a ballasting group, and when c represents 2 or more, each $R_6$ may be the same or different.

6. The process of claim 1, wherein the 4-arylthio-5-pyrazolone magenta coupler is represented by the formula

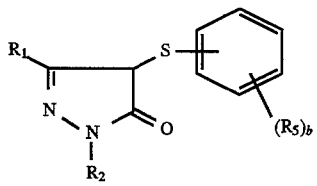

wherein $R_1$ represents an anilino group, an acylamino group or a ureido group, $R_2$ represents a phenyl group, $R_5$ represents hydrogen, alkyl, alkoxy, halogen, aryl, aryloxy, acylamino, sulfonamido, sulfamoyl, carbamoyl, arylsulfonyl, aryloxycarbonyl, alkoxycarbonyl, alkoxysulfonyl, aryloxysulfonyl, alkylureido, arylureido, nitro, cyano, hydroxyl or carboxy group, b represents an integer from 1 to 5, and when b represents 2 or more, each $R_5$ may be the same or different.

7. The process of claim 1, wherein the 4-arylthio-5-pyrazolone magenta coupler is represented by the formula

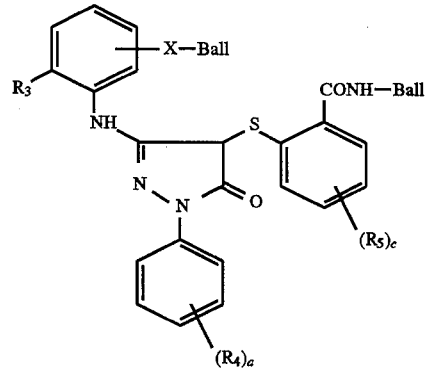

wherein a represents an integer from 1 to 5, $R_4$ represents hydrogen, alkyl, alkoxy, halogen, aryl, aryloxy, acylamino, sulfonamido, sulfamoyl, carbamoyl, arylsulfonyl, aryloxycarbonyl, alkoxycarbonyl, alkoxysulfonyl, aryloxysulfonyl, alkylureido, arylureido, nitro, cyano, hydroxyl or carboxy group, $R_3$ is halogen atom, alkyl or aryl group, X is a direct group or a linking group, Ball is a ballasting group of such size and configuration as to render a compound to which it is attached non-diffusible in photographic coatings, $R_5$ represents hydrogen, alkyl, alkoxy, halogen, aryl, aryloxy, acylamino, sulfonamido, sulfamoyl, carbamoyl, arylsulfonyl, aryloxycarbonyl, alkoxycarbonyl, alkoxysulfonyl, aryloxysulfonyl, alkylureido, arylureido, nitro, cyano, hydroxyl or carboxy group, c represents an integer from 1 to 4, and when a and c each represents 2 or more, each $R_4$ and $R_5$ may be the same or different.

* * * * *